US 9,498,371 B2

(12) United States Patent
Salama

(10) Patent No.: US 9,498,371 B2
(45) Date of Patent: Nov. 22, 2016

(54) FLOW CONTROL AND COLLECTION DEVICE

(71) Applicant: International Medical Technology, Inc., Temecula, CA (US)

(72) Inventor: Fouad A. Salama, Temecula, CA (US)

(73) Assignee: International Medical Technology, Inc., Temecula, CA (US)

( * ) Notice: Subject to any disclaimer, the term of this patent is extended or adjusted under 35 U.S.C. 154(b) by 246 days.

(21) Appl. No.: 13/827,453

(22) Filed: Mar. 14, 2013

(65) Prior Publication Data

US 2013/0197458 A1    Aug. 1, 2013

Related U.S. Application Data

(63) Continuation-in-part of application No. 13/031,379, filed on Feb. 21, 2011.

(51) Int. Cl.
| | |
|---|---|
| A61F 5/44 | (2006.01) |
| A61F 5/448 | (2006.01) |
| A61F 2/00 | (2006.01) |
| A61F 5/445 | (2006.01) |
| A61F 5/441 | (2006.01) |

(52) U.S. Cl.
CPC ............. *A61F 5/4405* (2013.01); *A61F 5/445* (2013.01); *A61F 5/448* (2013.01); *A61F 2/0013* (2013.01); *A61F 5/441* (2013.01); *A61F 2005/4455* (2013.01)

(58) Field of Classification Search
CPC ........... A61F 5/445; A61F 2005/4455; A61F 5/448; A61F 5/4405; A61F 5/451; A61F 5/441; A61F 2/0013

USPC .......................................................... 604/335
See application file for complete search history.

(56) References Cited

U.S. PATENT DOCUMENTS

| | | | |
|---|---|---|---|
| 3,900,795 A | | 8/1975 | Larsen et al. |
| 4,121,589 A | * | 10/1978 | McDonnell .................. 604/328 |

(Continued)

FOREIGN PATENT DOCUMENTS

EP        0 689 810 A2    1/1996

OTHER PUBLICATIONS

International Medical Technology, Inc., PCT/US2012/025225 filed Feb. 15, 2012, "Notification of Transmittal of The International Search Report and The Written Opinion of The International Searching Authority" mailed Jun. 20, 2012.

*Primary Examiner* — Tatyana Zalukaeva
*Assistant Examiner* — Ariana Zimbouski
(74) *Attorney, Agent, or Firm* — McKee, Voorhees & Sease PLC

(57) ABSTRACT

A flow control and collection system includes a flow control device having a tubular member in which an inflatable balloon is positioned about the circumference of the interior side wall for closing the passageway to movement of matter and liquid when the balloon is expanded and allowing flow when the balloon is contracted against the side wall to which it is attached. The flow control device includes an adapter at the outer end of the tubular member having one or more interlocking features. A generally outwardly extending flange may be configured at the outer end of the tubular member. The flange may be configured with an inflatable membrane having an inflated position wherein at least a portion of the inflatable membrane extends generally outwardly from the flange.

11 Claims, 12 Drawing Sheets

(56) References Cited

U.S. PATENT DOCUMENTS

| | | |
|---|---|---|
| 4,419,100 A | 12/1983 | Alexander |
| 4,799,929 A | 1/1989 | Knowles |
| 4,846,798 A | 7/1989 | Holtermann et al. |
| 4,911,699 A | 3/1990 | Fenton |
| 5,185,008 A | 2/1993 | Lavender |
| 5,242,373 A | 9/1993 | Scott et al. |
| 5,312,381 A | 5/1994 | Brooks |
| 5,647,861 A | 7/1997 | Steer et al. |
| 5,690,623 A | 11/1997 | Lenz et al. |
| 5,693,035 A | 12/1997 | Leise, Jr. et al. |
| 5,730,735 A | 3/1998 | Holmberg et al. |
| 5,947,941 A | 9/1999 | Leise, Jr. et al. |
| 6,135,986 A | 10/2000 | Leisner et al. |
| 6,328,719 B1 | 12/2001 | Holtermann et al. |
| 6,432,093 B1 | 8/2002 | Shiina |
| 6,485,476 B1 | 11/2002 | Von Dyck et al. |
| 6,659,988 B1 | 12/2003 | Steer et al. |
| 6,802,831 B2 | 10/2004 | Plass et al. |
| 7,001,367 B2 | 2/2006 | Arkinstall |
| 7,087,042 B2 | 8/2006 | Montgomery |
| 7,160,275 B2 | 1/2007 | Falconer |
| 7,179,245 B2 | 2/2007 | Giori |
| 7,468,056 B2 | 12/2008 | Burt |
| 7,553,273 B2 | 6/2009 | Ferguson et al. |
| 7,556,707 B2 | 7/2009 | Giori |
| 7,604,622 B2 | 10/2009 | Pedersen et al. |
| 2002/0077611 A1* | 6/2002 | von Dyck et al. ............ 604/333 |
| 2003/0236509 A1 | 12/2003 | Silvestrini |
| 2006/0206069 A1 | 9/2006 | Cline |
| 2007/0123832 A1 | 5/2007 | Cline et al. |
| 2007/0198034 A1 | 8/2007 | Ortiz et al. |
| 2008/0215001 A1 | 9/2008 | Cowe |
| 2009/0043151 A1* | 2/2009 | Gobel ............................ 600/31 |
| 2009/0216206 A1 | 8/2009 | Nishtala et al. |
| 2009/0227970 A1 | 9/2009 | Nishtala et al. |
| 2009/0227971 A1 | 9/2009 | Nishtala et al. |
| 2009/0247969 A1 | 10/2009 | Nishtala et al. |
| 2010/0022976 A1* | 1/2010 | Weig ............................ 604/355 |
| 2010/0069859 A1 | 3/2010 | Weig |
| 2010/0174253 A1 | 7/2010 | Cline et al. |
| 2010/0222754 A1 | 9/2010 | Nishtala et al. |
| 2010/0280489 A1 | 11/2010 | Nishtala et al. |
| 2011/0092929 A1* | 4/2011 | Weig ............................ 604/338 |
| 2011/0306823 A1* | 12/2011 | Gobel et al. .................... 600/32 |

* cited by examiner

FLOW CONTROL AND COLLECTION DEVICE

CROSS REFERENCE TO RELATED APPLICATION

This application is a Continuation-in-Part application of U.S. Ser. No. 13/031,379 filed Feb. 21, 2011, herein incorporated by reference in its entirety.

BACKGROUND OF THE INVENTION

Persons requiring ileostomy or colostomy procedures or being incontinent have need for a flow control and collection device that will not leak or accidentally separate, and is simple to install, operate and remove.

SUMMARY OF THE INVENTION

The flow control and collection device of this invention meets the needs of persons having had an ileostomy or colostomy procedure to address incontinency issues, or are fecally incontinent. The flow control and collection devices of this invention can be positioned in a body opening such as a stoma or around the anus. For example, persons requiring a colostomy or ileostomy have need for a flow control and collection device of the present invention.

In one aspect of the invention, a flow control and collection system for human excretions is disclosed. The flow control device includes a tubular member having inner and outer ends interconnected by a passageway adapted for insertion into a body opening. An adapter at the outer end of the tubular member has one or more interlocking features. A collection bag that has a sealed body and at least one opening also includes an adapter having one or more counterpoising interlocking features to removably lock the device and bag adapters together.

A device providing flow control for human excretions is also disclosed. The device includes a tubular member having inner and outer ends connected by a passageway and the inner end adapted for insertion into a body opening. An adapter is included at the outer end of the tubular member having a plurality of radially spaced interlocking features formed in the adapter.

A bag for collecting human excretions is also disclosed. The bag includes a sealed body having at least one opening and an adapter attached to the body around the opening. The adapter includes a generally planar surface and a plurality of radially spaced interlocking features. The interlocking features removably lock the bag to a device having an inner end adapted for insertion into a body opening.

In another aspect of the invention, a flow control device for human excretions is disclosed. The device includes a tubular member having inner and outer ends interconnected by a passageway. The tubular member has a discontinuous side wall and the inner end of the tubular member is adapted for surgical attachment at a body opening. The device also includes a plurality of tube diameter adjustment points spaced opposite one another on opposing sides of the discontinuity in the side wall and a tether between opposing adjustment points to adjust the diameter of the passageway to the size of the body opening.

DETAILED DESCRIPTION OF THE PREFERRED EMBODIMENTS

Figure 1:
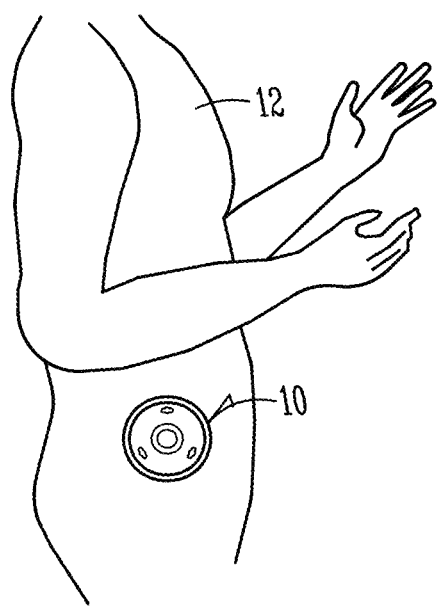
FIG. 1 is a fragmentary side view of a flow control device of this invention being positioned in a body opening of a person.

The flow control device of this invention is referred to generally in FIG. 1 by the reference numeral 10 and is shown positioned in a body opening, such as a stoma, on a the side of a person 12. The device 10 may be positioned in another body opening, such as the rectum of the person 12. The device 10 may be used, for example, by those having had a colostomy or ileostomy.

Figure 2A:
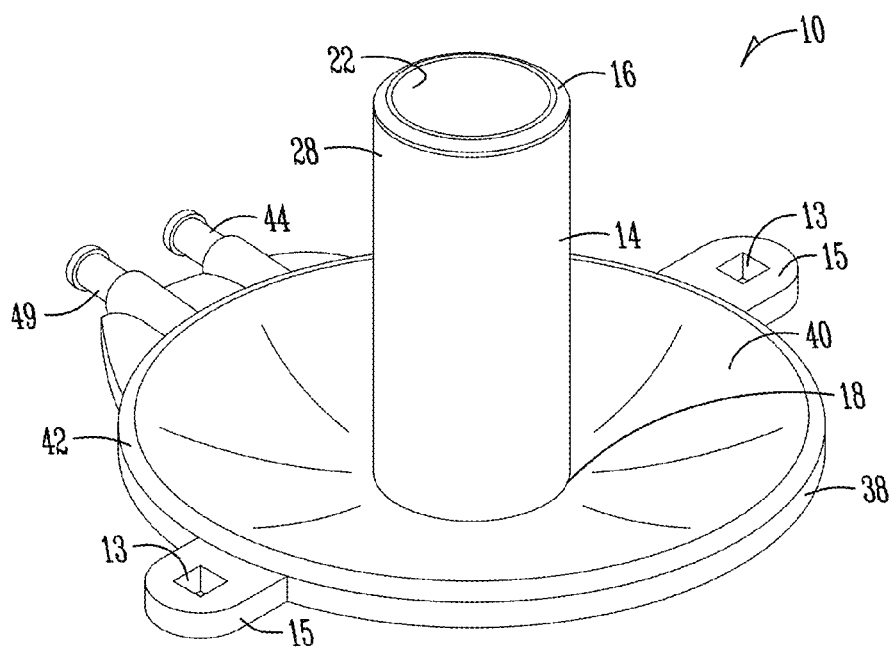
FIGS. 2A-B are perspective views of embodiments of the flow control device shown in FIG. 1.
Figure 2B:
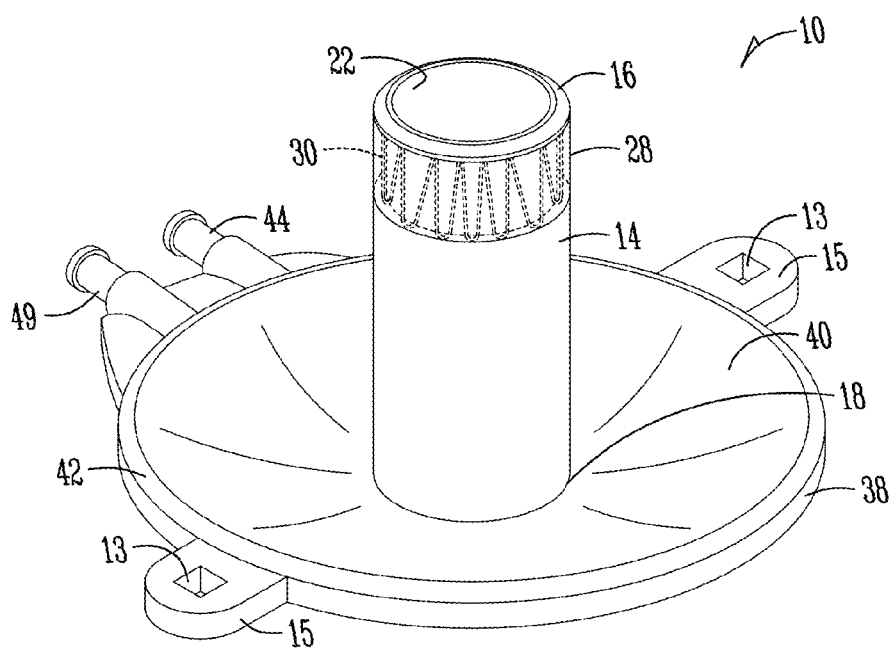

In FIGS. 2A-B, the flow control device 10 includes a tubular body member 14 having inner and outer ends 16 and 18, and on opposite sides of a body opening 19 (see FIG. 3) when installed. The tubular body member 14 may include one or more wall stiffeners to support the tubular member 14 against collapsing. In one aspect of the invention, the tubular member 14 includes an internal wall stiffener such as a rigid tube enclosed by the inner and outer skins of the tubular member 14. One example of a rigid tube includes polycarbonate tubing, or other tubing of sufficient strength to prevent the tubular member 14 from collapsing. Other types of stiffeners include the wire frame 30 discussed below. A wafer 40 in the form of a flange is connected to the outer end 18 of the tubular member 14. The inner surface 40 of wafer 42 may include a concave profile, with the depth of the profile decreasing from proximate the outer end 18 of the tubular member 14 outward to the outer peripheral edge of the wafer 42. The concavity of the inner surface 40 of wafer 42 prevents the inner surface 40 of wafer 42 from compressing or putting pressure on the tissue or mucosa 17 around the body opening 19, such as would be present in the case of a colostomy or ileostomy. A device adapter 38 is included on the side of wafer 42 opposite the inner surface 40 and further described below. The device adapter 38 includes a pair of ears 15 extending generally perpendicularly outward from the from the outer peripheral edge of the adapter 38. Each ear 15 includes an attachment point 13, such as a hole extending through the ear 15. A ileostomy or colostomy belt, such as are well known in the art, may be used to strap the device 10 to the person 12 by hooking ends of the belt to the attachment points 13.

Figure 3:
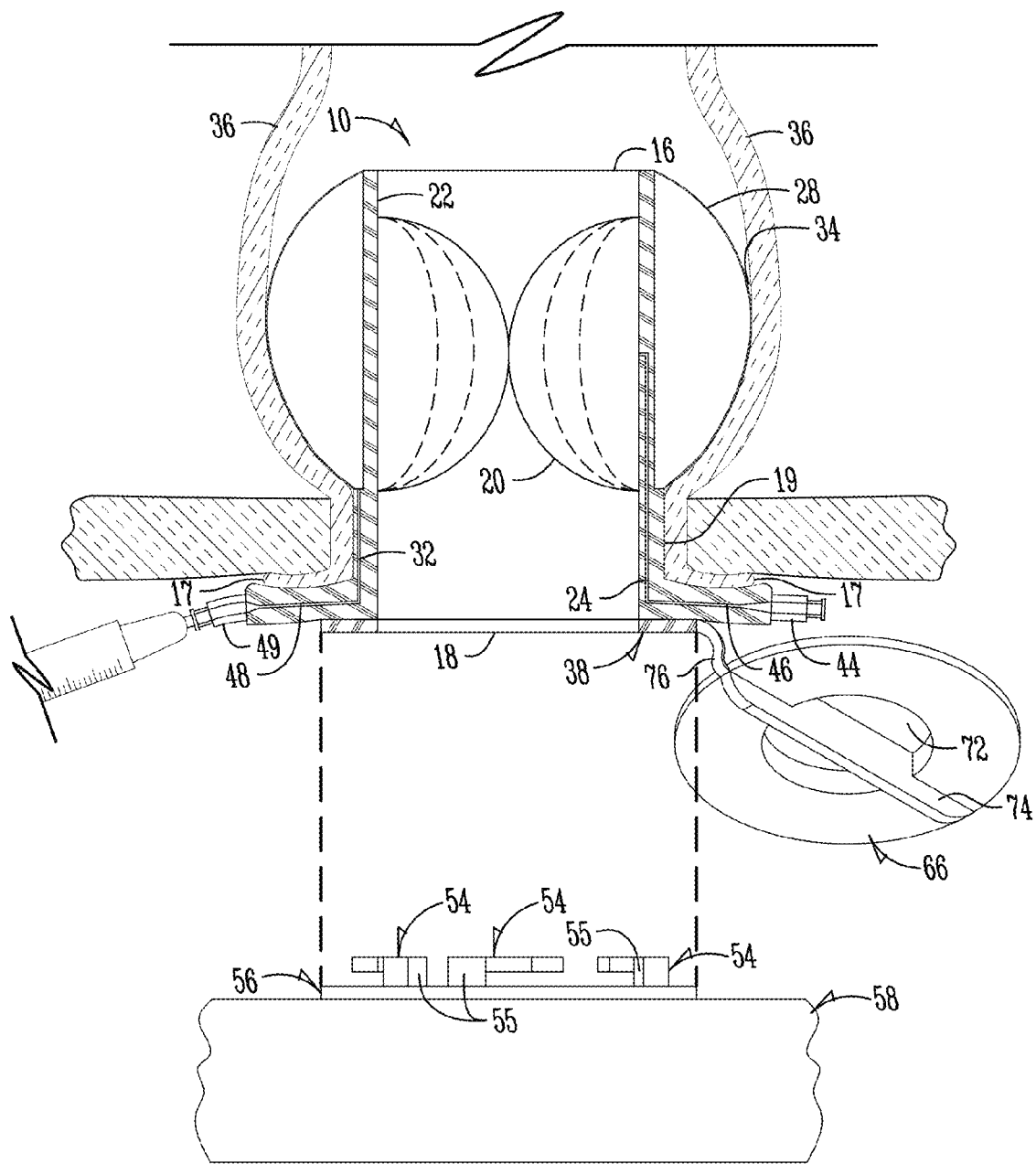
FIG. 3 is a cross-sectional view of a flow control device positioned in a body opening.

In FIG. 3, a balloon valve 20 is attached to the interior side wall 22 of the tubular member 14 and is inflated and deflated through a passageway 24 in the tubular member side wall 22. The balloon valve 20 is attached radially (i.e., 360 degrees) about the interior side wall 22 of the passageway 24. When the valve 20 is inflated, the balloon expands radially inward away from the interior side wall 22 of the passageway 24 toward the center of the passageway 24 in sealing engagement with itself. The balloon valve 20 seals closed the passageway 24 to prevent the flow of matter and fluid through the passageway 24 when the balloon valve 20 is inflated. The balloon valve 20 of the present invention is shown and described in a commonly owned application, application Ser. No. 11/464,686 filed Aug. 15, 2006, incorporated by reference herein in its entirety.

An expandable membrane 28 is attached at the inner end 16 of the tubular member 14, and in one aspect of this invention the interior side wall 22 is supported against being collapsed when the membrane 28 is inflated by a wire frame 30 (see FIG. 2B). The wire frame 30 is preferably positioned within the interior side wall 22 or secured to the interior side wall 22 to provide stiffness and rigidity to at least that portion of the side wall 22 supporting the pressure resulting from expansion of the expendable membrane 28 as shown in FIG. 3. In the case where the body opening 19 is generally smaller (e.g., such as with an ileostomy opening or chronic colostomy patients) the wire frame 30 may be collapsed or pinched to reduce the diameter of the inner end 16 of the tubular member 14 to facilitate insertion within a smaller body opening. The wire frame 30 may be configured to hold the collapsed position for an increment of time (e.g., the time needed to fully insert the inner end 16 in the body opening 19) and resume or expand to its original, pre-collapsed position after the increment of time has elapsed. For example, the wire frame 30 may include a memory which causes it to return to its original, pre-collapsed position from a collapsed or pinched position. After insertion of the device 10 and the wire frame 30 resuming its original, pre-collapsed position, the wire frame 30 supports the interior side wall 22 or tubular member 14 against collapsing when the expandable membrane 28 is inflated. In one aspect of the invention, the wire frame 30 comprises a nickel titanium alloy, such as Nitinol, having one or more memorized positions. The wire frame 30 may also be stainless steel, such as surgical grade stainless steel. Embodiments of this invention using the expandable membrane 28 with or without the wire frame 30 are contemplated. For example, the device 10 could include other types of stiffeners, such as those discussed above, to prevent the tubular member 14 from collapsing. As passageway 32 in the side wall of the tubular member 14 connects with the expandable membrane 28, the pressure applied to the expandable membrane 28 may of course vary as required to form a seal at the interface 34 between the expandable membrane 28 and the interior wall 36 surrounding the body opening 19 and retain the device 10 in the opening 19. For example, in the case of a colostomy or ileostomy, the expendable membrane 28 may be expanded to form a seal at the interface 34 between the interior wall surface 36 of the intestine and the expendable membrane as shown in FIG. 3.

Figure 4:
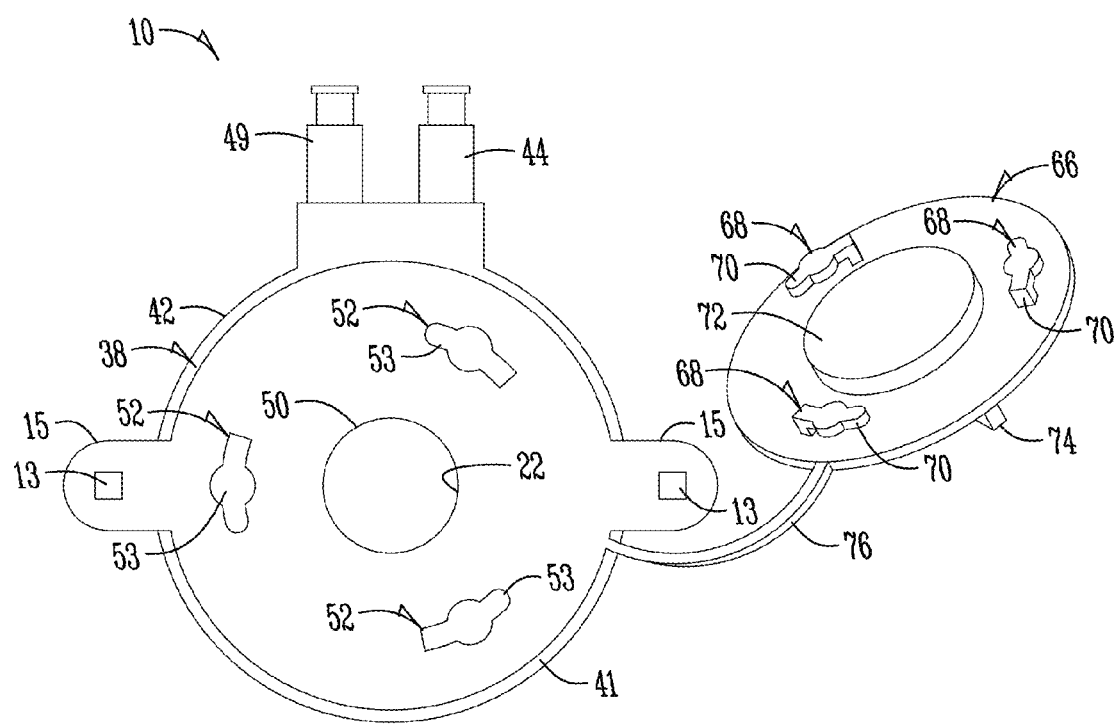
FIG. 4 is an end elevation view of the flow control device.

In FIG. 4, a device adapter 38 is provided either in the wafer 42 or attached to the outer end 18 of the tubular member 14, or attached to the outer surface 41 of wafer 40. The device adapter 38 or wafer 42 includes laterally outwardly extending tube portions 46 and 48 terminating at our near the outer peripheral edge of the wafer 42 or bag adapter 38 in self-sealing micro valves 44 and 49, such as check valves (see FIG. 3). The tube portions 46 and 48 connect respectively to passageway 24 and 32 in the side wall 22 for inflating and deflating the balloon valve 20 and expandable membrane 28 respectively, using for example a syringe. The device adapter 38 has a generally planar outer surface and includes an aperture 50 coinciding with the outer end 18 of the tubular member 14. Spaced radially in, on or through the device adapter 38 is a plurality of interlocking features 52. In a preferred form of this invention, the interlocking features 52 include one or more geometries that provide a twist and lock type connection. In one aspect, the interlocking features 52 include a plurality of keyways 53 radially spaced about the aperture 50 in the device adapter 38.

The device 10 may include a cap 66 having counterpoising interlocking feature 68 radially spaced about a plug 72 sized to occupy the aperture 50 in the device adapter 38 when the cap 66 is secured to the device adapter 38. The counterpoising interlocking features 68 preferably include a plurality of one or more geometries configured to interlock, such as by use of a twist and lock action, with the interlocking features 52 of the device adapter 38 by gripping the rib 74 on the flow control device cap 66, joining the interlocking features 52 and 68 together, and twisting the cap 66 to lock the cap 66 to the device adapter 38. In one aspect of this invention, the counterpoising interlocking feature 68 on the cap 66 include a plurality of keys 70 radially spaced about plug 72. The keys 70 provide a male contact having geometries commensurate with the counterpoising female contacts configured in the device adapter 38 so that the keys 70 are received within the keyways 53 to removably lock cap 66 over the aperture 50 of device adapter 38. A tether 76 may be included on the device adapter 38 attached to cap 66 for keeping it tethered to the adapter 38 when not in use. The interlocking features 52 and 66 in the adapter 38 and cap 66 prevent the cap from inadvertently or accidently becoming separated from the adapter 38. This invention contemplates that the female or male configuration of the interlocking features 52 and 68 may be switched between the adapter 38 and the cap 66.

Figure 5:
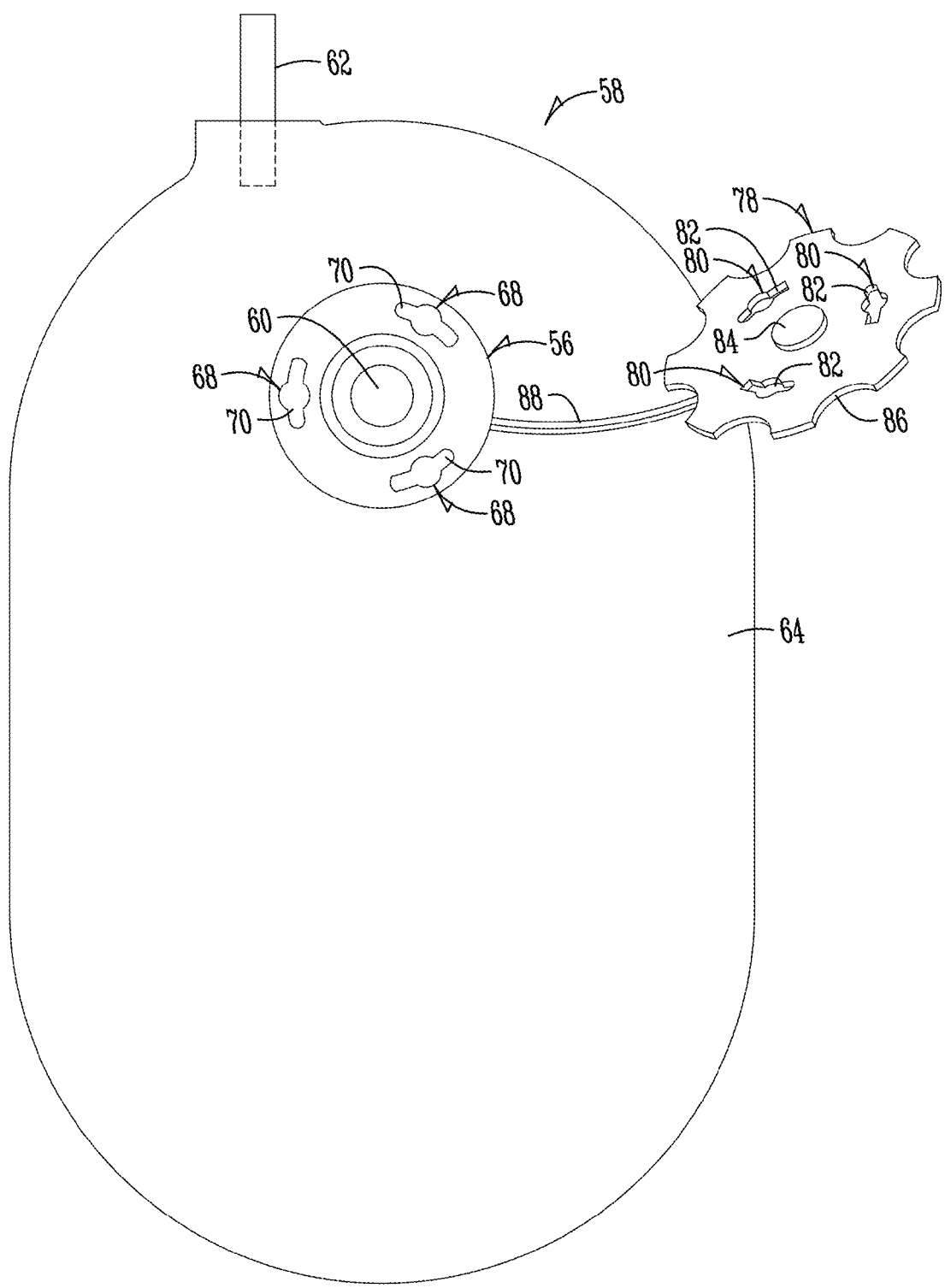
FIG. 5 is a front elevation view of a collection bag of this invention.
Figure 6:
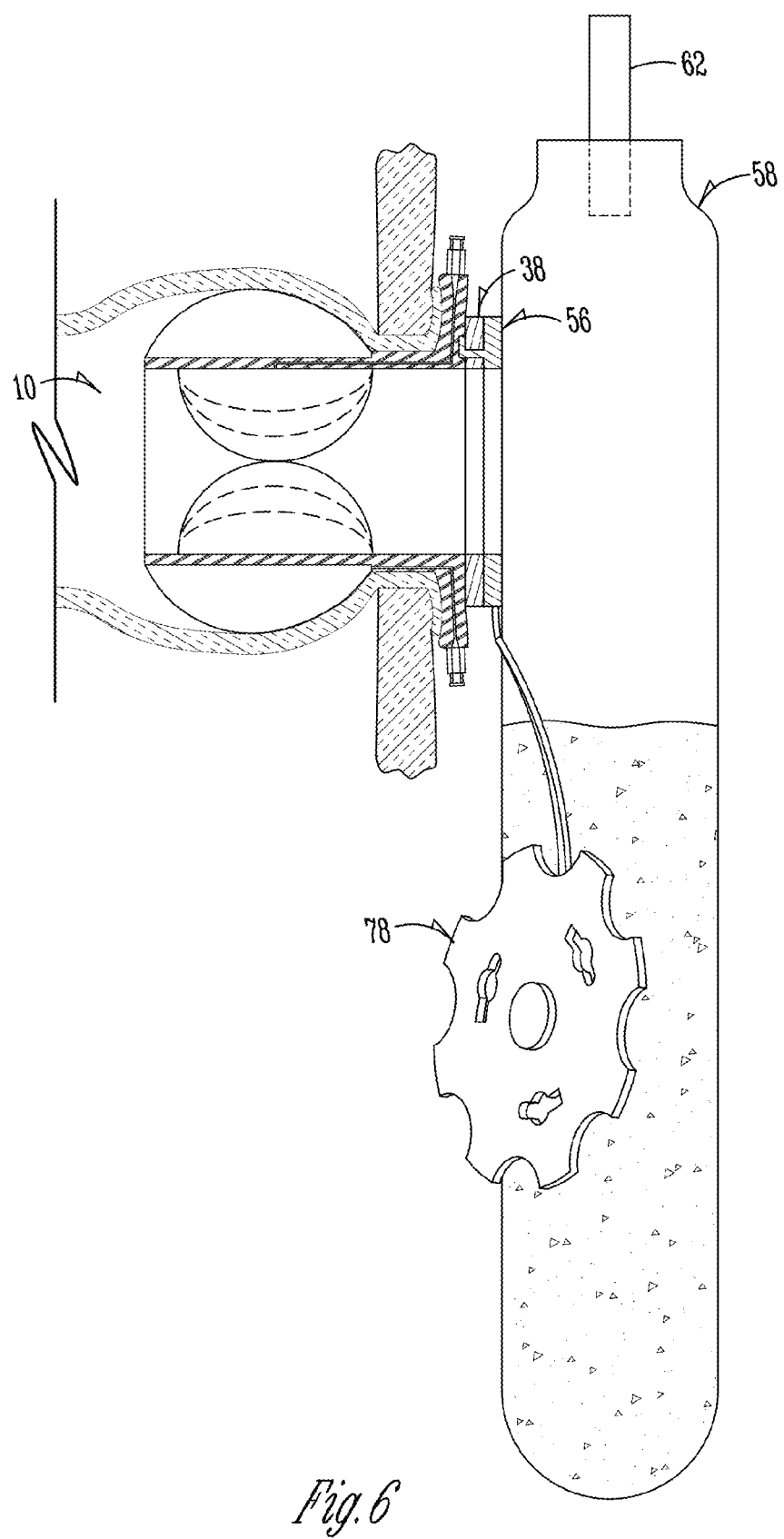
FIG. 6 is a view similar to FIG. 3 but showing adapters connecting the flow control device and waste collection bag.

A waste collection bag 58 is illustrated in FIGS. 5-6. The waste collection bag 58 is formed of a disposable sealed body 64. The sealed body 64 may include a vent 62 for allowing gases to vent from the body. The bag 58 also includes a central opening 60 surrounding circumferentially by a bag adapter 56. The bag adapter 56 is a generally planar wafer-shaped member and may be included in or attached to the sealed body 64 of the bag 58. The bag adapter 56 is also preferably a semi or fully rigid component, and hence constructed of a semi or fully rigid material. The adapter 56 is preferably more rigid than the bag 58 material. Spaced radially about opening 60 either in or on the bag adapter 56 is a plurality of counterpoising interlocking features 68. In one aspect of this invention, the features 68 include a plurality of keys 70 radially spaced about opening 60. The keys 70 are raised a distance off the surface of the adapter 56 to provide a gap between the key and the adapter surface as best illustrated in FIG. 3. The key 70 may include one or more geometries providing a twist and lock function when inserted through a plurality of corresponding keyways, such as the keyways 53 illustrated in the device adapter 38 shown in FIG. 4 or the plurality of keyways 82 shown in the bag cap 78. Although the keys 70 illustrate a specific embodiment of the counterpoising interlocking feature 68 of the present invention, other interlocking features are contemplated. For example, various male and corresponding female features or contacts are contemplated that would allow for a twist and lock function whereby the adapters and caps of the present invention are removably locked together. In another aspect of the invention, the waste collection bag 58 includes a cap 78 that may, in one example, be secured by a tether 88 to the bag adapter 56. The cap 78 includes a plug 84 extending generally perpendicularly and outwardly from the surface of the cap 78 and having a diameter corresponding to the opening 60 in the bag adapter 56. Radially spaced about the plug 84 is a plurality of interlocking features 80. The interlocking features 80, in one aspect of the invention, comprise keyways 82 configured in the bag cap 78. The outer peripheral edge of the cap 78 may include one or more cogs 86 to facilitate gripping, manipulating and turning the cap 78 into a removably locked position onto the bag adapter 56. This is accomplished by aligning the keys 70 of the bag adapter 56 with the keyways 82 in the cap 78, inserting the keys 70 through the keyways 82, and rotating the bag cap 78 either clockwise or counterclockwise depending upon the orientation of the keys 70 on the bag adapter 56. When the cap 78 is removably locked to the bag adapter 56, the plug 84 occupies the spaced defined by opening 60 in the bag adapter 56. The bag 58 is thereby sealed and may be disposed of Gas venting membranes may be included within vent 62, or in a vent-type plug 84. The membrane may comprise a charcoal filter for filtering and deodorizing gases escaping from the bag 58. In another aspect of the invention, the waste collection bag 58 includes an entirely sealed body 64 having only the single opening 60 in the bag adapter 56. The bag cap 78 includes a filter, such as for example within an opening in the plug 84, to allow gases to escape from the bag 58 through the opening in the plug 84. As illustrated in FIG. 6, the bag adapter 56 mates flush with the device adapter 38 on the flow control device 10. The counterpoising interlocking feature 68 of the bag adapter 56 engage the interlocking features 52 in the device adapter 38. The bag 58 is rotated to thereby removably lock the adapters 56 and 38 together, thereby placing the flow control device 10 in communication with the opening 60 in bag 58. The balloon valve 20 is deflated and waste material and fluids are permitted to flow from the body through the flow control device 10 into the waste collection bag 58. The balloon valve 20 is reinflated to close the device 10 and the waste collection bag 58 is disconnected from the flow control device 10; the flow control device cap 66 may also be used to cap off the flow control device 10.

Figure 7:
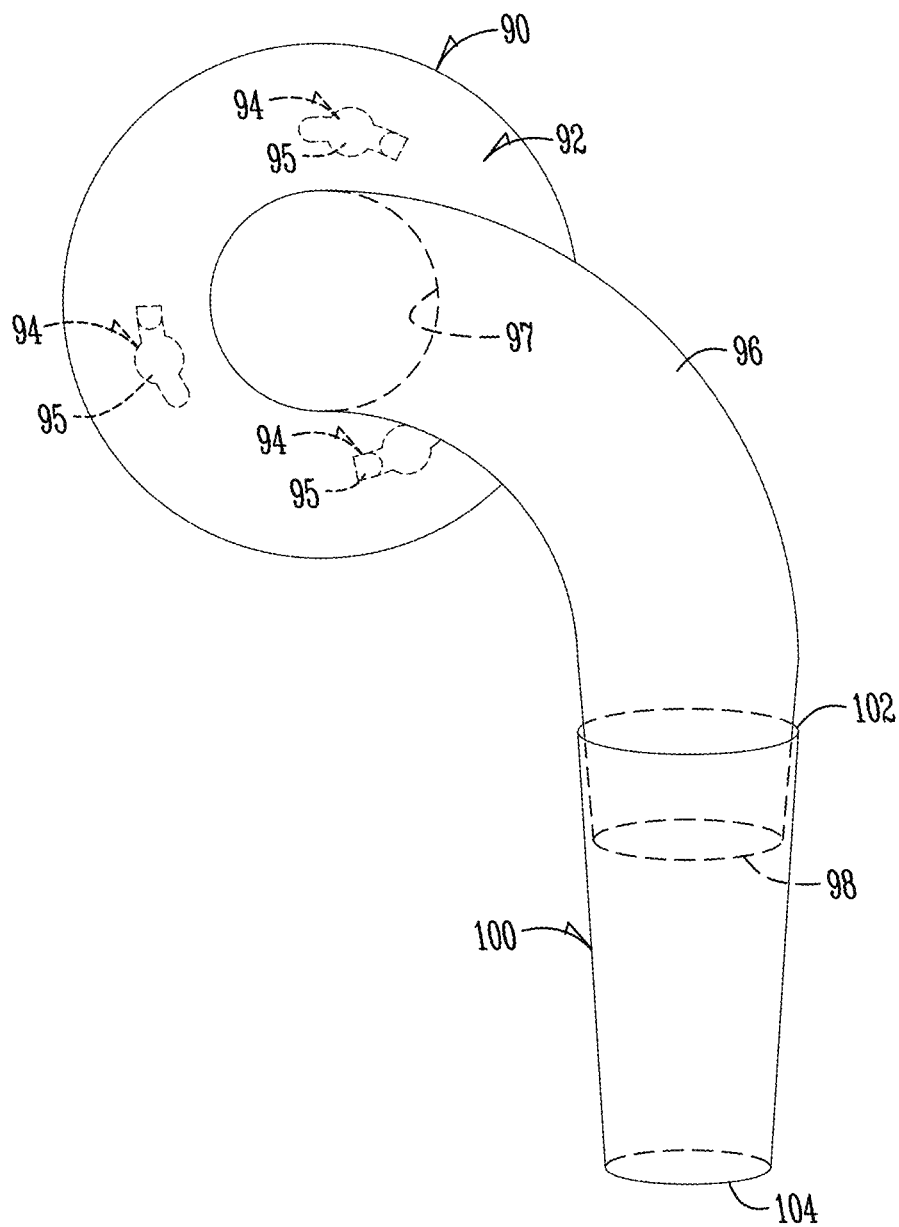
FIG. 7 is a perspective view of a bagless device of this invention.

A bagless device 90 suitable for removable attachment to the flow control device 10 is shown in FIG. 7. The bagless device 90 includes an adapter 92 having a plurality of counterpoising interlocking features 94 radially disposed about the opening 97. In one aspect of this invention, the counterpoising interlocking feature 94 comprises keyways 95 similar to those discussed above. The bagless device 90 includes an outwardly and downwardly extending tube 96 having an opening or inlet 97 and an outlet end 98. The outlet end 98 is tapered, having a generally smaller diameter than the inlet end 97. A degradable tubular sleeve 100 is provided having an inlet opening 102 and an outlet opening 104. The inlet opening 102 may have a diameter generally larger than the outlet end 98 of tube 96 but smaller than the overall average diameter of the tube 96 so as to form a friction fit between the inlet opening 102 of the degradable tubular sleeve 100 and the outlet end 98 of tube 96 when the inlet opening 102 of the sleeve 100 is slid over the outlet end 98 of tube 96. The sleeve 100 may have the same diameter inlet opening 102 as the outlet opening 104 so that the inlet opening 102 is slightly deformed, such as by stretching, to secure it to the outlet end 98 of tube 96. In use, the counterpoising interlocking features 94 mate with the interlocking features 52 of the device adapter 38 (illustrated in FIG. 4). Thus, the bagless device 90 twists and removably locks to the flow control device 10 to allow material and fluid to pass through the flow control device 10, flange tube device 90 and disposable tubular sleeve 100. The sleeve 100 is sufficiently flexible to allow manipulation of the outlet opening 104 to a desired location for dispensing waste material and fluids into a device such as a toilet when standing or seated. The tubular sleeve 100 may be disposed of after each use and the flange tube device 90 cleansed and sanitized for subsequent use.

Figure 8:
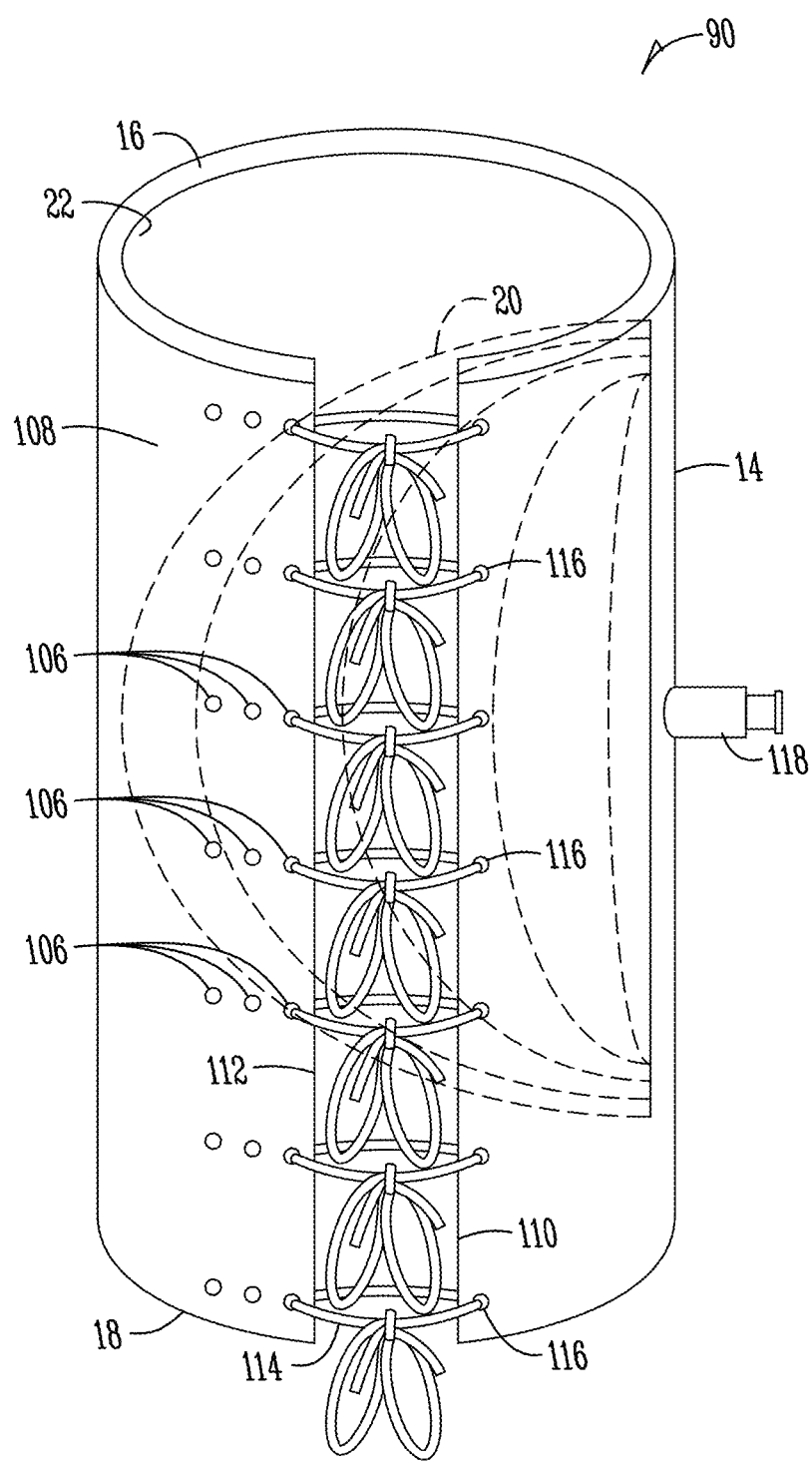
FIG. 8 is a perspective view of another flow control device of this invention for surgical attachment at a body opening.

FIG. 8 discloses another aspect of the present invention. The flow control device 10 illustrated in FIG. 8 includes a tubular member 14 with an opening passing through the entirety of the side wall 108 to allow the diameter of the tubular member 14 to be adjusted to a larger or smaller opening diameter at the inner end 16 and/or outer end 18. Opposing sides 110 and 112 of the side wall 108 include a column of eyelets 116 proximate side 110 and a plurality of adjustment points 106 comprising a plurality of eyelets 116 generally adjacent the opposing side 112. The eyelets 116 and adjustment points 106 on opposing sides 110 and 112 of the side wall 108 are configured generally horizontal relative to each other. A plurality of tethers 114, such as surgical suture, pass through the eyelets 116 and adjustment points 106 to drawn the opposing sides 110 and 112 of the side wall 108 together depending upon the desired size of the opening for the inner end 16 of tubular member 14. Adjustment points 106 allow the diameter of the tubular member 14 to be increased or decreased accordingly. The interior side wall 22 of the tubular member 14 includes a balloon valve 20, as previously discussed, in communication with a passageway terminating externally in a check valve 118. In use, the inner end 16 of the flow control device 10 is surgically attached about a body opening, such as the rectum of the person. Depending upon the size of the rectum of the individual, proper adjustments are made to the diameter of the inner end 16 of tubular member 14 to encircle the rectum with the inner end 16 of the flow control device 10. Tethers 114 are adjusted to size the tubular member 14 accordingly. Inflation and deflation of the balloon valve 20 provides obstruction to and passage of matter and fluids passing from the rectum.

Figure 9A:
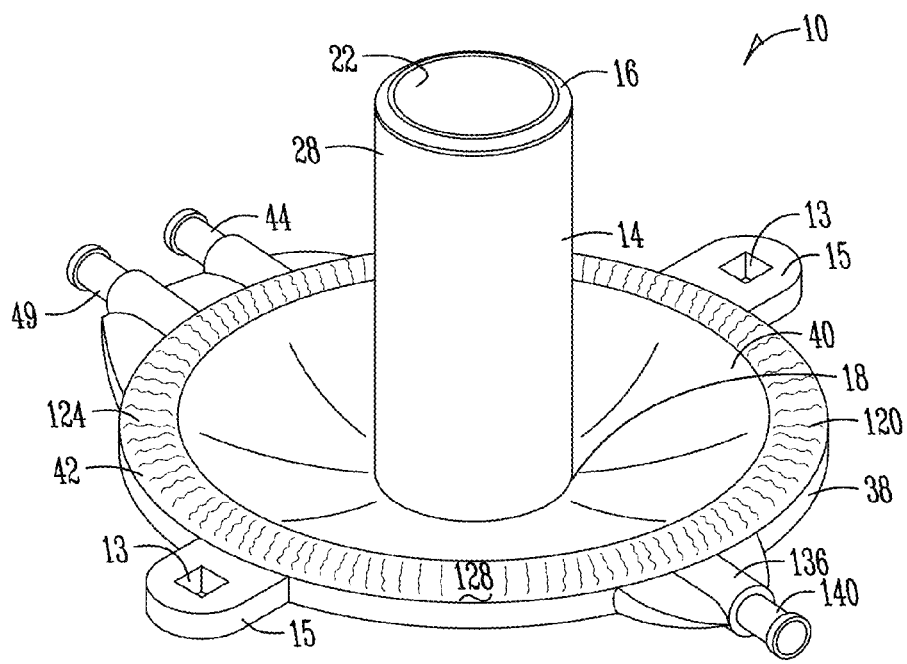
FIGS. 9A-B are perspective views of another embodiment of the flow control device according to exemplary aspects of the present invention.
Figure 9B:
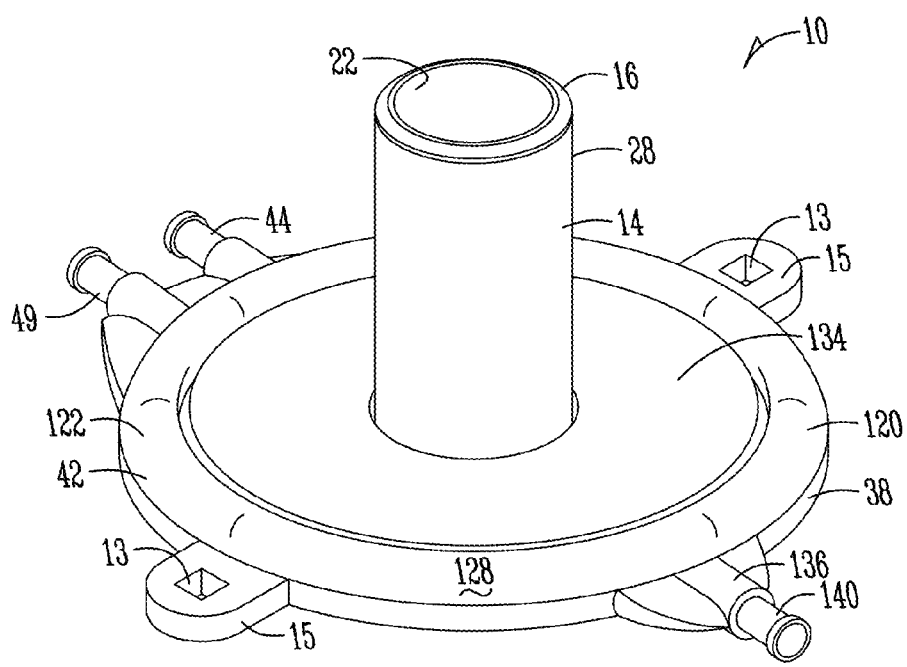
Figure 10A:
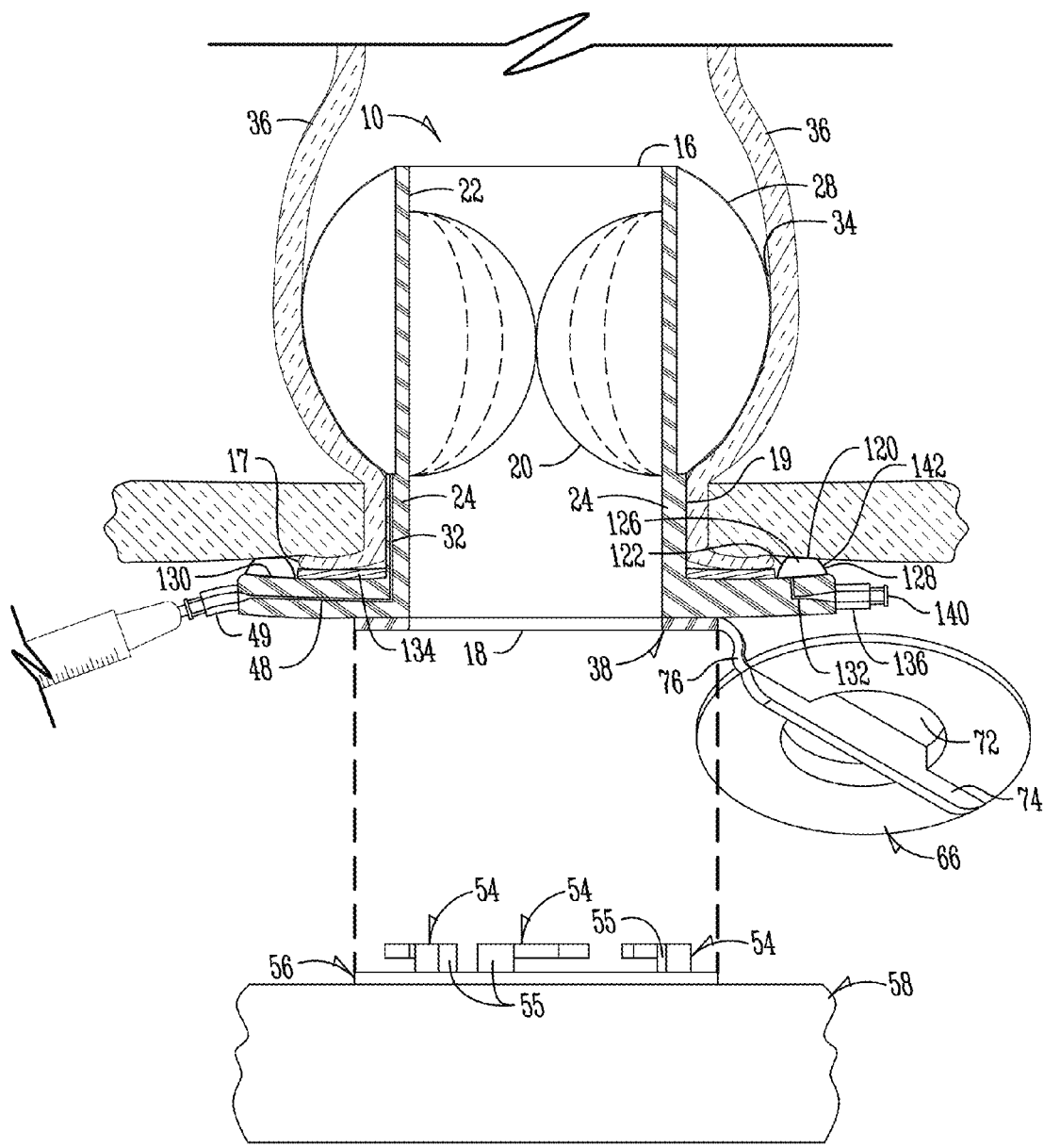
FIGS. 10A-C are cross-sectional views of various embodiments of the flow control device shown in FIGS. 9A-B.
Figure 10B:
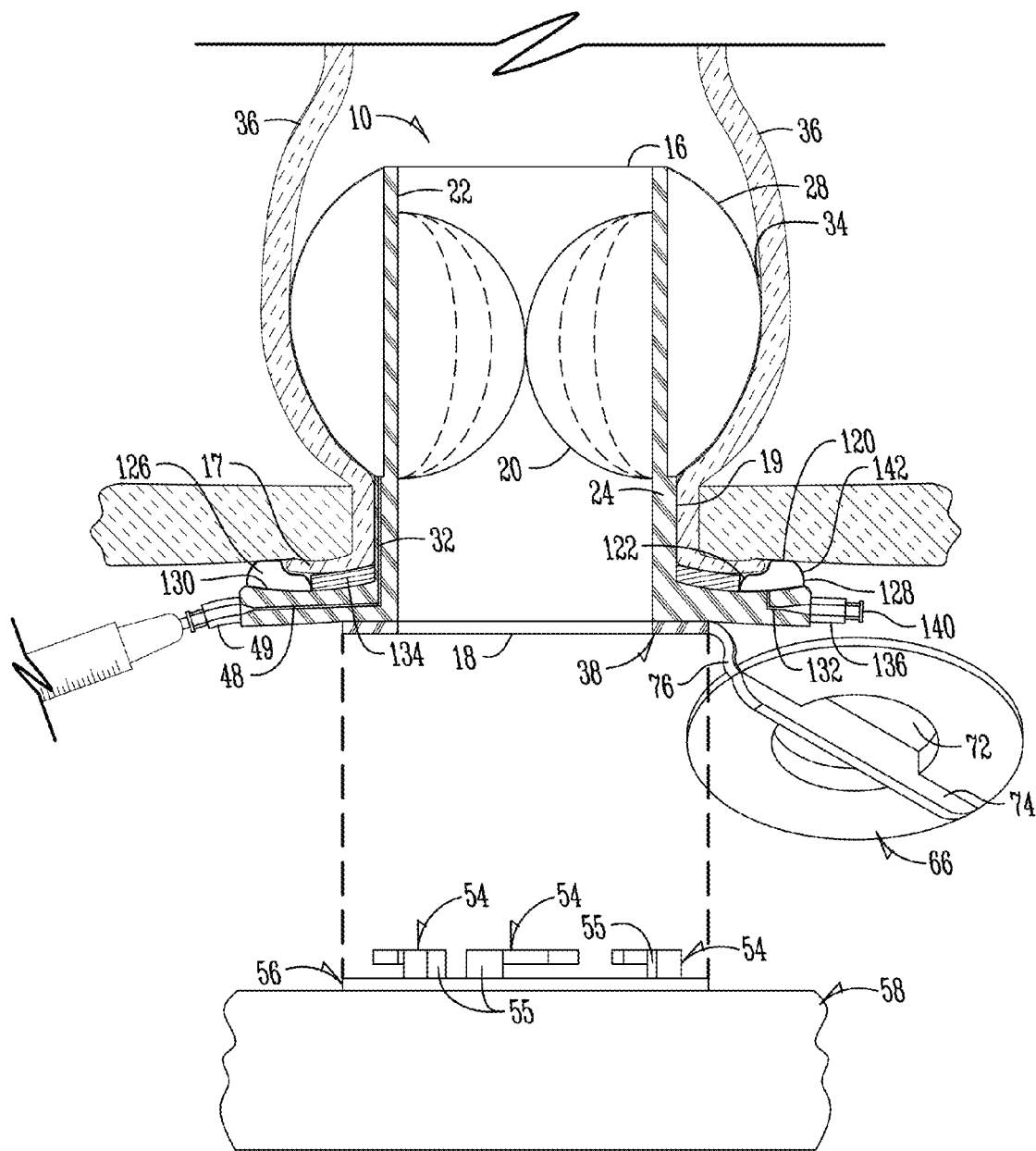
Figure 10C:
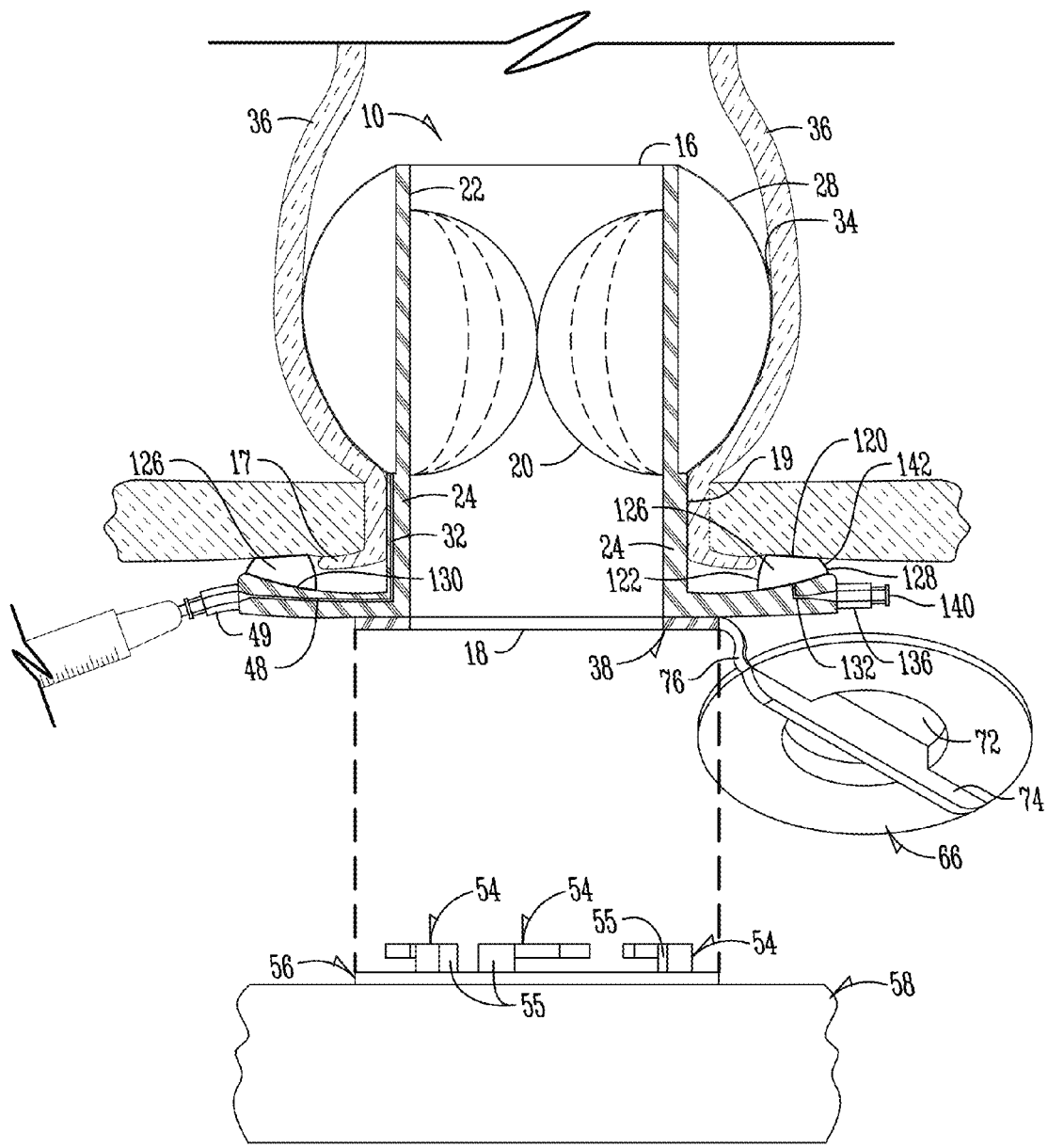

FIGS. 9A-B are perspective views of other embodiments of the device according to exemplary aspects of the present invention. The flow control device includes a tubular body member 14 having inner and outer ends 16 and 18, respectively. The tubular member 14 may include one or more wall stiffeners as a coating, embedded or internal structure or support. The material portion of the tubular body member 14 may include stiffeners or may be constructed of a stiffer or more rigid material than other parts of the flow control device 10. A wafer 40 in the form of a flange is connected to the outer end 18 of the tubular member 14. The inner surface 40 of the wafer 42 may be configured to include a concave profile, with the depth of the profile decreasing from proximate the attachment point of the outer end 18 to the wafer 42 to the outer peripheral edge of the wafer 42. A device adapter 38, such as the one illustrated in FIG. 4, is included on the side of the wafer opposite the inner surface 40. The device adapter 38 includes a pair of ears 15 extending generally perpendicularly outward from the outer peripheral edge of the adapter 38. Each ear 15 may be configured to include an attachment point 13, such as a hole extending through the ear. An ileostomy or colostomy belt, such as are well-known in the art, may be used to strap the device 10 to a person by hooking ends of the belt to the attachment point 13. A balloon valve 20 is also configured within the interior side wall 22 of the tubular member and is inflatable and deflatable through a passageway 24 in the tubular member sidewall 22. The balloon valve 20 is attached radially about the interior sidewall 22 of the passageway 24. When the balloon valve 20 is inflated, the balloon expands radially inward away from the interior sidewall 22 of the passageway 24 toward the center of the passageway 24 in sealing engagement upon itself. The balloon valve 20 seals closed the passageway 24 to prevent the floor of matter and/or fluid through the passageway 24 when the balloon valve 20 is inflated. A balloon valve having a configuration and function as described is detailed in a commonly owned application, application Ser. No. 11/464, 686 filed Aug. 15, 2006, incorporated by reference herein in its entirety. An expandable membrane 28 is also configured and attached at the inner end 16 of the tubular member 14. A passageway 32 in the sidewall of the tubular member 14 connects with the expandable membrane 28. The expandable membrane 28 may be moved between an expanded and contracted or an inflated and deflated position by inserting air or fluid into the expandable membrane 28 through the passageway 32 and removing the air or fluid from the expandable membrane 28 through the passageway 32. The device adapter 38 or wafer 42 includes laterally outwardly extending tube portions 46 and 48 terminating at or near the outer peripheral edge of the wafer 42 or bag adapter 38 in self-sealing micro valves 44 and 49, such as check valves (see FIG. 3). The tube portions 46 and 48 connect respectfully to passageway 24 and 32 in the sidewall 22 for inflating and deflating the balloon valve 20 and expandable membrane 28 respectfully, using for example a syringe. The device adapter 38 has a generally planar outer surface and includes an aperture 50 coinciding with the outer end of the tubular member 14. A plurality of interlocking features 52 are spaced radially in, on or through the device adapter 38. In a preferred form of the invention, the interlocking features include one or more geometries that provide a twist-and-lock type connection. The device adapter 38 is configured to receive any of the aforementioned features of the present invention using any of the aforementioned interlocking configurations. As illustrated specifically in FIGS. 9A-B, the inner surface 40 of the wafer 42, such as for example, near the outer peripheral edge of the wafer 42 or at the outer peripheral edge of the wafer 42 may be configured with an expandable membrane 120 configured to be expanded from a deflated position 124 shown in FIG. 9A to an inflated positioned 122 shown in FIG. 9B. The outer surface 128 of the expandable membrane 120 may be configured of the inter surface 40 of the wafer 42 or of a separate material designed into, fused or configured into the inner surface 40 of wafer 42. The expandable membrane 120 may also be configured within the wafer 42 underneath the inner surface 40 and the inner surface 40 configured with an expandable type material to allow the expandable membrane 120 to expand the inner surface 40 outward away from the inner surface 40 or outer surface 41. Defined within the expandable membrane 120 is a volume 126 spaced between the outer surface 128 of the expandable membrane 120 and an inner surface 130. Depending upon the configuration of the expandable membrane 120, the inner surface 130 may be configured of the inner surface 40 of the wafer 42, an interior surface of the wafer 42 or the outer surface 41 of the wafer 42. The device adapter 38 or wafer 42 may be configured to include an outwardly extending tube portion 136 at or near the outer peripheral edge of the wafer 42 or bag adapter 38. The outwardly extending tube portion 136 may be configured to include a self-sealing micro valve such as illustrated in FIGS. 10A-C. The tube portion 136 is connected in communication with the self-sealing micro valve 140 and the expandable membrane 120. Using, for example, a syringe, air or fluid may be introduced through the micro valve 140 into the expandable membrane 120 through the outwardly extending tube portion connected in communication with the expandable membrane 120. Similarly, air or fluid contained within the expandable membrane 120 may be released or withdrawn from within the volume 126 of the expandable membrane 120 through the outwardly extending tube portion 136 and self-sealing micro valve 140. The volume 126 of the expandable membrane 120 may be filled with air or liquid to expand the expandable membrane 120 to a desired stiffness or inflated position 122 as illustrated in FIG. 9B. For example, the expandable membrane 120 may be filled to a volume sufficient to lift or push the inner surface 40 of the wafer 42 away from the abdominal wall so no pressure is applied on the stoma or any protruded part of the intestine. The expandable membrane 120 by operation as previously described, may be deflated from the inflated position 122 to a deflated position 124 as illustrated in FIG. 9A. The outwardly extending tube portion 136 may be configured with a passageway 132 placing the self-sealing micro valve 140 in communication with the volume 126 of expandable membrane 120 as best illustrated in FIGS. 10A-C. An medically suitable absorbent, such as an medical grade absorbent material, may be positioned to rest against the inner surface 40 of the wafer 42 as shown in FIG. 9B in the space between the inner surface 40 of the wafer 42 and the abdominal wall as shown in FIG. 10A.

FIGS. 10A-C provide illustrations of the flow control device 10 in use which use has been previously set forth and described in the preceding descriptions. While in use, the expandable membrane 120 may be inflated from the deflated position 124 shown in FIG. 9A to the inflated positions shown in FIGS. 10A-C. In the inflated position 122, the expandable membrane 120 elevates the inner surface 40 of the wafer 42 off of the tissue or mucosa 17 around the body opening 19, such as would be present in the case of a colostomy or ileostomy. Lifting the inner surface 40 of the wafer 42 from off of the tissue or mucosa 17 around the body opening 19 helps prevent the inner surface 40 of the wafer 42 from compressing or putting pressure on the tissue or mucosa 17 around the body opening 19. The expandable membrane 20 in the inflated position 122 presses the outer surface 128 against the skin (see FIG. 10C) to create a seal between the inner surface 40 of the wafer 42 and the body opening 19 to provide another seal to prevent fluid and/or matter from leaking out of the body opening 19 around the interface between the flow control device 10 and the body opening 19. Additionally, with the expandable membrane 28 expanded to secure the device 10 within the opening the expandable membrane 120 also provides an additional securing feature to help fully secure and lock the device 10 in place at the body opening 19, especially in cases where the abdominal wall is irregular. For example, with the expandable membrane 28 inflated within the body opening 19 and the expandable membrane 120 expanded without the body opening 19 the device 10 is fully secured in position by clamping down on, pinching down on, or compressing against safe portions of the skin around the opening and within the opening to prevent inadvertent dislodgment, loss of or extraction of the control device from the body opening while maintaining a seal against material and/or fluid leakage from around the interface between the device 10 and the body opening 19. Therefore, according to one aspect of the invention, increasing the size of the expandable membrane 120 may serve to pull on the expandable membrane 28 to anchor the device 10 in place, while sealing the stoma from the inside to prevent leakage. As shown in FIG. 10A, an absorbent 134 may be placed between the wafer 42 and the abdominal wall to absorb any fluid or other material that might leak. The absorbent 134 may be changed out or replaced as needed.

The expandable membrane 120 may be configured in various shapes and sizes occupying a portion, a substantial portion or a lesser portion of the inner surface 40 of the wafer 42. The expandable membrane 120 may be configured to occupy an outer peripheral edge of the wafer 42 and a portion of the inner surface 40 in another configuration. FIGS. 10A-C illustrate various configurations for the expandable membrane 120. As illustrated in FIG. 10A, the expandable membrane may be configured to occupy a portion of both the outer peripheral edge and the inner surface 40 of the wafer 42. For example, the outer surface 128 of the expandable membrane 120 may be configured so that in the inflated position 122 it is spaced away from contact with a very outer edge of the tissue or mucosa 17 around the body opening 19. Thus, inflation of the expandable membrane 120 to the inflated position 122 presses against the skin to create separation between the tissue or mucosa and the expandable membrane 120 thereby creating a seal between the interface of the device and the body opening to prevent inadvertent leakage of fluid and/or matter. In another embodiment, as illustrated in FIG. 10B, the outer surface 128 of the expandable membrane 120 may be configured to have multiple elevations such as a step-shaped surface where, for example, a portion of the outer surface 128 is pressed away from resting against the outermost portion of the tissue or mucosa 17 around the body opening 19 while the outermost portion of the outer surface 128 of the expandable membrane 120 presses firmly against the skin. Thus, for example, the outer profile as shown in FIG. 10B of the outer surface 128 of the expandable membrane 120 may be wedge shaped so that the volume of the expandable membrane 120 in the inflated position 122 increases toward the outer peripheral edge of the wafer 42. Such a configuration of the expandable membrane 120 may assist in providing a seal against the skin to prevent leakage around the outermost surface of the tissue or mucosa 17 around the body opening 19 as well as the around the wafer 42 thereby providing a double seal to prevent any type of leakage of fluid or matter from the interface between the device 10 and the body opening 19. An absorbent 134, as previously discussed and described, may also be placed in the space between the tissue or mucosa around the body opening 19 and the inner surface 40 of the wafer 42 to absorb fluid or other leakage. In another exemplary configuration as illustrated in FIG. 10C, the expandable membrane 120 may be configured so that the outer surface 128, in the inflated position 122, is in sealing contact with the skin around the body opening 19. The volume 126 of the expandable membrane 120 may be configured so that the inner surface of the wafer 42 is completely lifted off of or away from the tissue or mucosa 17 immediately around the body opening to keep the inner surface 40 of the wafer 42 from compressing or putting pressure on the tissue or mucosa 17 immediately around the body opening 19. The expandable membrane 120 may be configured with an outer surface 128 have an large sealing surface in contact with the skin to provide added protection against leakage. The inner surface 40 of the wafer 42 may be sloped or angled to create a sizable gap or separation between the inner surface 40 of the wafer 42 and the tissue or mucosa 17 around the body opening 19. In the configuration illustrated in FIG. 10C, the outer surface 128 seals against the skin in the inflated position 122 to prevent any inadvertent or unwanted leakage of fluid and/or matter from the interface between the device 10 and the body opening. As previously indicated the aforementioned embodiments illustrated, for example, in FIGS. 10A-C serve to seal off the device to prevent any leakage from the body at the interface between the device 10 and the body opening 19. The embodiments of the expandable membrane 120 also elevate the inner surface 40 of the wafer 42 from off of the tissue or mucosa 17 immediately around the body opening to prevent any unnecessary unwanted compression or pressure on the tissue or mucosa. These embodiments also provide a secondary mechanism for securing the flow control device 10 in place within the body opening 19 when used in combination with the expandable membrane 128. For example, the expandable membrane 28 provides a seal between the interface of the device 10 and within the body and the expandable membrane 120 provides a seal at the interface between the outer surface 128 of the expandable membrane 120 outside the body. These two sealing mechanisms, in addition to sealing off the device to prevent any inadvertent or untended leakage of fluid and/or matter, also serve to secure and lock the device in place to prevent any inadvertent movement, dislodgement or loss of the device 10 from the body opening 19.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. A flow control device adapted for insertion into a body opening having an inner surface and an outer surface, the device comprising:
    a tubular member having an inner circumference opposite an outer circumference, an inner end and an outer end interconnected by a passageway adapted for passing fluid or waste therethrough;
    a flange extending outwardly from the tubular member proximate to the outer end, the flange having a width defined between a peripheral edge and the outer circumference of the tubular member; and
    an inflatable membrane disposed on an inner surface of the flange and extending inwardly from the peripheral edge towards the outer circumference of the tubular member for a portion comprising less than the width of the flange, the inflatable membrane configured to be in contact with the outer surface of the body opening.

2. The flow control device of claim 1 wherein the inflatable membrane is inflatable when installed on the body.

3. The flow control device of claim 1 further comprising an absorbent disposed on the inner surface of the flange for a portion separate from the portion occupied by the inflatable membrane.

4. The flow control device of claim 2 further comprising an inflation valve in communication with the inflatable membrane.

5. The flow control device of claim 1 wherein the inner surface moves from the deflated to inflated position in a direction generally toward the inner end of the tubular member.

6. The flow control device of claim 1 wherein the flange comprises a generally convex profile.

7. A flow control device for human excretions comprising:
    a tubular member having an inner circumference opposite an outer circumference, a passageway, and an inner end and an outer end configured to be disposed on opposite sides of an opening in a human body;

an inflatable balloon valve attached radially within the tubular member proximate to the inner end;

an inflatable membrane extending radially outward from an exterior surface of the tubular member proximate to the inner end;

a flange extending outwardly from the tubular member and terminating at an outer perimeter;

an inflation valve disposed on the flange proximate to the outer perimeter and fluidly connected to the inflatable membrane; and an expandable seal extending towards the outer circumference of the tubular member from the outer perimeter of the flange and comprising a portion of an inner surface of the flange less than a distance between the outer circumference of the tubular member and the outer perimeter, Wherein the expandable seal is adapted to seat around the opening to seal the opening against leakage.

8. The flow control device of claim 7 wherein the expandable seal is inflatable when installed within the opening of the human body.

9. The flow control device of claim 7 further comprising an absorbent removably disposed on the inner surface of the flange and positioned between the tubular member and the expandable seal.

10. The flow control device of claim 7 wherein the expandable seal extends to a peripheral edge of the flange.

11. The flow control device of claim 7 wherein the expandable seal further comprises a flange contact surface and a skin contact surface, wherein the skin contact surface is step-shaped.

* * * * *